United States Patent [19]

Zappia et al.

[11] Patent Number: 4,764,603
[45] Date of Patent: Aug. 16, 1988

[54] STABLE SALTS OF S-ADENOSYL-L-METHIONINE WITH POLYANIONS

[75] Inventors: Vincenzo Zappia; Mario De Rosa, both of Naples, Italy

[73] Assignee: Gibipharma S.p.A., Pero, Italy

[21] Appl. No.: 764,240

[22] Filed: Aug. 9, 1985

[30] Foreign Application Priority Data

Feb. 14, 1985 [IT] Italy .............................. 19512 A/85

[51] Int. Cl.⁴ ..................... A61K 31/70; C07H 19/167
[52] U.S. Cl. ........................................ 536/26; 536/24; 536/27
[58] Field of Search .................... 536/26, 27

[56] References Cited

PUBLICATIONS

Allan et al., Can. J. Microbiol., 26, pp. 912–920, 1980.
Miller, Can. J. Microbiol., 30, pp. 236–246, 1984 (Feb.).
Aldrich Catalog Handbook of Fine Chemicals, 1984, Aldrich Chem. Co., Milwaukee, Wis., pp. 1400–1401.
March, Advanced Organic Chemistry, McGraw-Hill, New York, 1968, p. 489.

*Primary Examiner*—Ronald W. Griffin
*Assistant Examiner*—L. Eric Crane
*Attorney, Agent, or Firm*—Bruce M. Collins

[57] ABSTRACT

Stable salts of S-adenosyl-L-methionine with water-soluble polyanions, such as polyphosphates, polyvinylsulfonates -sulfates or -phosphates, polyacrylates, polystyrene sulfonates, are described.

The salts according to the invention, prepared by precipitation from aqueous solutions of pH not exceeding 3.5, possess peculiar stability, solubility, nonhygroscopicity and are valuable for use as active constituents in pharmaceutical compositions.

12 Claims, 1 Drawing Sheet

( □ ) SAM-CHLORIDE;

( ■ ) $SAM^+HSO_4^- - H_2SO_4 - 2CH_3 C_6 H_4 SO_3 H$;

( O ) SALT OF EXAMPLE 1;

( ● ) SALT OF EXAMPLE 3;

( ▲ ) SALT OF EXAMPLE 4;

( ✱ ) SALT OF EXAMPLE 5;

( △ ) SALT OF EXAMPLE 6;

( ◢ ) SALT OF EXAMPLE 7;

( ◁ ) SALT OF EXAMPLE 9;

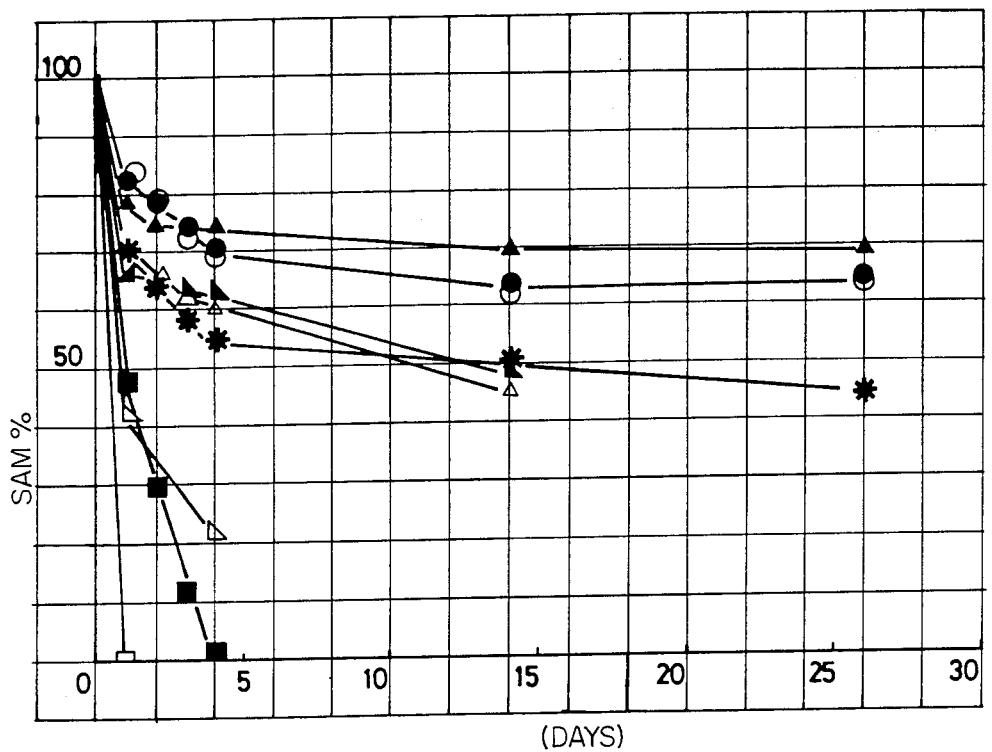
- (□) SAM-CHLORIDE;
- (■) $SAM^+\text{-}HSO_4^-\text{-}H_2SO_4\text{-}2CH_3C_6H_4SO_3H$;
- (○) SALT OF EXAMPLE 1;
- (●) SALT OF EXAMPLE 3;
- (▲) SALT OF EXAMPLE 4;
- (✱) SALT OF EXAMPLE 5;
- (△) SALT OF EXAMPLE 6;
- (◂) SALT OF EXAMPLE 7;
- (◭) SALT OF EXAMPLE 9;

STABLE SALTS OF S-ADENOSYL-L-METHIONINE WITH POLYANIONS

This invention relates to novel, stable salts of the S-adenosyl-L-methionine (SAM) with water-soluble polyanions, to processes for obtaining them, and to therapeutic formulations containing said novel salts as their active constituents.

The substance S-adenosyl-methionine, currently known as SAM and ubiquitarily occurring in living organisms, performs a number of important biochemical functions: (a) it acts as a methyl group donor in a large number of transmethylation reactions; (b) it is a substrate of a specific lyase that converts the molecule to methylthioadenosine (MTA) and homoserine; (c) it functions as an aminobutyric chain donor to tRNA; (d) it is an aminoacidic chain donor in the biosynthesis of biotin; (e) it is a donor of the adenosyl moiety; (f) it is a promoter of lysine-2,3-amino mutase, threonine synthetase, pyruvate formate lyase, and $N^5$-methyltetrahydrofolate-homocysteine methyltransferase; (g) it is an inhibitor of H ribonuclease, methylene tetrahydrofolic reductase, and ethanolamianephosphate cytidyltransferase; (h) it is required for bacterial and leukocyte chemotaxis; and (i) it is required in the prokaryote and eukaryote restriction and modification system of the DNA. Moreover, the decarboxylate product thereof, the S-adenosyl-(5')-3-methylthiopropylamine (deca-SAM) acts as a propylamine group donor in the biosynthesis reactions of polyamines. There exists a recent exhaustive literature dealing with these multiple biological roles of SAM and deca-SAM (Zappia V. et al., "Biomedical and Pharmacological roles of Adenosyl-methionine and the Central Nervous System", page 1, Zappia V. et al., Eds., Pergamon Press. N.Y., 1979; Paik W. K. et al., "Protein Methylation", Maister A. Ed., J. Wiley & Sons N.Y., 1980; "Biochemistry of S-Adenosylmethionine and Related Compounds", Usdin E. et al. Eds., MacMillan Press L.t.D., 1982). In particular, SAM, as a methyl donor in transmethylations, leads to the biosynthesis of a broad range of metabolites to form, for example, N—$CH_3$ (creatine, choline, N-methylnicotinamide, adrenaline, many alkaloids, proteins, nucleic acids), S—$CH_3$ (methionine, S-methylmethionine), O—$CH_3$ (methanephrine, lignin, pectine, phenols), C—$CH_3$ (C28-ergosterol, thymine riboside, certain antibiotics, proteins, nucleic acids, and polysaccharides) bonds. The variety of compounds and chemical bonds created by the enzymatic transmethylations show that these play multiple physiological roles; we may remember among them the detoxication function that is performed in, for example, the methylation of pyridine and its derivatives, such as nicotinic acid and the amide therof. Methylation frequently also can alter the physiological properties of molecules: suffice it to consider the differences between noradrenaline and adrenaline, morphine and codeine, etc. (Borchardt R. T., "Enzymatic Basis of Detoxication", Vol. II, page 43, Academic Press, 1980). Of significant interest was the discovery of a number of methylated bases occurring in tRNA. In connection with this, various assumptions were put forward about regulating functions possibly performed by methylations of polynucleotides (Kersten H., "Biochemistry of S-Adenosylmethionine and Related Compounds", page 357, Usdin E. et al. Eds., Mac Millan Press L.t.D., 1982). Also of importance are the methylation reaction of proteins, the subject matter of several research works carried out in the last years by W. K. Paik, and colleagues.: (a) the guanidine residues of arginine, with formation of $\omega$-N-methylarginine; (b) the amino groups of the lysine residues, with formation of $\epsilon$-N-mono- and dimethyl-lysine; (c) the carboxy groups of the residues of dicarboxylic amino acids to form methylesters.

The methylation of lysine residues of proteins will, in addition to having functional significance for the proteins themselves, also results in the production of N-trimethyl-lysine. This methylated amino acid is an intermediate in the biosynthesis of carnitine. In addition to the transmethylation reactions, the other metabolic direction in which SAM plays a basic role involves the biosynthesis of polyamines. In this biogenetic route, following to enzymatic decarboxylation, SAM acts as a donor of the propylamine group to putrescine and spermidine to form spermidine and spermine, respectively, the primary biological polyamines occurring in eukaryotes. (Zappia V. et al., J. Biol. Chem. 7276, 225, 1980). Not only is the biosynthesis of polyamines correlated with the transmethylation reactions on account of the utilization of a common substrate to both the routes, but also because the deca-SAM, a decarboxylation product of SAM, is an inhibitor of the transmethylation reactions (Zappia V. et al., J. Biol. Chem. 244, 4499, 1969). Reported by the same authors is a similar inhibiting effect from MTA. In addition to the reactions where SAM acts as a substrate, there are to be mentioned certain regulation functions performed by the sulfonium compound, as for example, the regulation role played by SAM in the methylation of homocysteine to methionine. Here, in fact, while $N^5$-methyltetrahydrofolic acid will act as a methyl donor in the reaction, and vitamin $B_{12}$ is the methylated intermediate, SAM is, on the other hand, required in catalytic concentrations, as a methylation initiator of $B_{12}$. Another regulation role played by the sulfonium compound is its influence on the ethanolamine cytidyltransferase enzyme. A mechanism controlling the activity of this enzyme has, in fact, been anticipated and will probably involve a nonenzymatic methylation of the protein. The same mechanism was also anticipated for explaining the irreversible inactivation of the H ribonuclease from calf thymus gland which is exercised by SAM (Zappia V. et al. "Biomedical and Pharmacological Roles of Adenosylmethionine and the Central Nervous System", page 1, Zappia V. et al. Eds., Pergamon Press N.Y., 1979). Also of importance are the metabolic relationships of trans-sulfuration reactions, cycle of folate, and transmethylations, with one another.

Sam, after giving up the methyl group, is converted to S-adenosyl-homocysteine (SAH) which is a powerful inhibitor of all the transmethylation reactions that have been studied hitherto. Therefore, the enzymes that degrade SAM, one L-amino acid oxidase and one specific hydrolase, indirectly play a regulating role in the methyl transfer reactions. Though balance of the hydrolysis reactions is shifted towards condensation, SAH is subject to undergo hydrolysis all the same, because of the reaction products being removed in an enzymatic way. Adenosine is, in fact, quickly converted to inosine, hypoxanthine, xanthine, and it is excreted as uric acid, whereas homocysteine is metabolized by two competitive systems: the trans-sulfuration system which leads to cysteine, and the so-called "sulfur conservation cycle" which is joined again on the folate.

Owing to its multiple and complex biochemical functions, SAM is capable of exerting a number of pharmacologic effects, as summarized in the annexed Table 1.

SAM is easily obtained on an industrial scale, from yeasts grown on methionine-containing media (Cantoni G. L., "Methods in Enzymology", 3, 600, 1967).

The formula presented below, that represents the natural, biologically active form of adenosylmethionine (Zappia V. et al., Biochem. Biophys. Acta 178, 185, 1969) or the 5'-[[(3S)-3-amino-3-carboxy-propyl]methyl-(S)-sulfone]-5'-deoxyadenosine, symbolized (−)SAM, gives the $pK_a$ values for different ionizable groups of the molecule (Farooqui J. et al., "Electrophoresis" 4, 261, 1983).

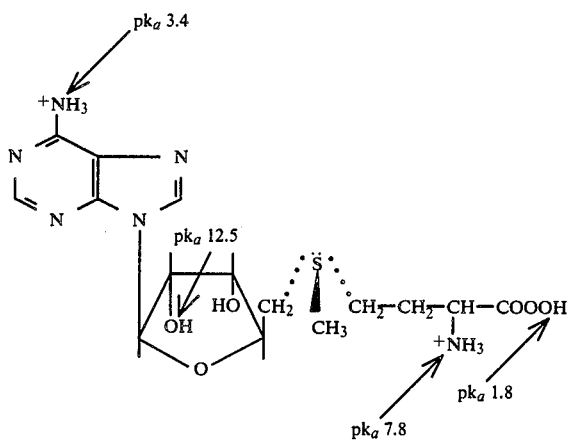

1983). At higher pH, the stability in solution is low and the molecule is quickly degraded according to different mechanisms. Stability of the salts of SAM as crystalline solids is critically controlled by the characteristics of the anion present; in particular, it is observed that increased steric hindrance of the anion improves stability of the solid phase molecule. In this case too, the predominant degrading mechanism leads to formation of MTA. One of these salts having the formula SAM$^{+-}$HSO$_4$H$_2$SO$_4^-$CH$_3$C$_6$H$_4$SO$_3$H (U.S. Pat. No. 3,954,726 of May 4, 1976) finds application in pharmacology at present.

It has now been found that salts of SAM with anion-type, water-soluble polyelectrolytes have good characteristics that are such as to render them particularly suitable both for use in pharmaceutical formulations and for preparative applications.

The state of charge of SAM at pH of up to 3.5 is, in fact, such as to ensure a stable and specific interaction of the molecule with the negatively charged sites of anion-type, water-soluble polyelectrolytes.

As a result of this interaction, insoluble salts will form, the stoichiometry of which may depend on several factors such as (a) the ratio of the reactants; (b) the pH and the nature of the reaction medium; (c) the chemical nature of the polyanion. In most cases studied, the stoichiometric ratios of the precipitated salts, defined as mols of SAM/g-equivalents of polymer, range from 0.5 to 0.1.

A particularly preferred ratio, on account of the stability of the salt obtained and for preparative considerations, is of 1:3 mol of SAM:equivalents of polyanion. On the other hand, also stoichiometries other than this

TABLE 1

| | Pharmacologic Effects of S—Adenosylmethionine | |
|---|---|---|
| EFFECTS | TEST MODEL | USE IN CLINICAL PATHOLOGY |
| ANTI-INFLAMMATORY | ACUTE EDEMA FROM CARRAGEENIN AND WHITE OF EGG CHRONIC EDEMA IN ARTHRITIS FROM ADJUVANTS | OSTEOARTHRITIS (improves muscular spasms, etc.) |
| ANALGESIC | PAIN FROM MYOTASIS (stretching of a muscle) | OSTEOARTHRITIS |
| HEPATOPROTECTIVE | STEATOSIS FROM HYPERLIPIDIC AND HYPERPROTEINIC DIET STEATOSIS FROM ACUTE INTOXICATION CAUSED BY ALCOHOL OR HEPATOTOXIC AGENTS (CARBON TETRACHLORIDE, BROMOBENZENE) | ACUTE AND CHRONIC DISEASES OF THE LIVER |
| BILE FLUIDIFYING | INTRAHEPATIC OR ESTROGEN-INDUCED BILE SUPERSATURATION CHOLESTASIS | GRAVIDIC CHOLESTASIS CHOLESTASIS CAUSED BY TREATMENT WITH ESTROGENS |
| ENHANCING OR STRENGTHENING (THE ACTION OF LEVODOPA) | — | PARKINSON'S DISEASE (IMPROVES AKINESIA AND RIGIDITY) |
| SLEEP INDUCING | — | DISORDER OF SLEEP MECHANISM OR OF WAKING-SLEEPING RHYTHM |
| ANTIDEPRESSANT | — | REDUCES OR RESOLVES SYMPTOMATOLOGY IMPROVES THE PSYCHO-AFFECTIVE SPHERE IN ATHEROSCLEROSIS |

Besides determining the state of charge, the pH also effects the chemical stability of the molecule in solution; sufficiently acid media and low temperatures prevent SAM from quickly degrading to essentially MTA. This degrading process is due to a nucleophilic, intramolecular attack of the carboxylic carbon on the aminoacidic γ methylene which is rendered particularly reactive by the nearby pole of sulfonium (Zappia V. et al., "Transmethylation", Usdin E. et al. Eds., Elsevier N.Y., 1979; Zappia V. et al., "Methods in Enzymology", 94, 73, ratio, namely in the above range of from 0.1 to 0.5, as mol of SAM/equivalent of the polymer, are compatible with the precipitation process and can be obtained by using either an excess or a deficiency of the polyanion with respect to SAM.

In salts having a lower stoichiometric ration than 0.3, the electroneutrality of the precipitate is attained because of cations in the medium acting as counterions on the polyanion together with SAM, whereas in salts having a higher ratio, anions in the medium neutralize in part the positive charges of the sulfonium compound.

Broadly speaking, the anions of strong and weak polyacids are a source of formation of insoluble salts of SAM. Representative examples of strong acid-derived polyanions are polymers or copolymers which contain in the macromolecular backbone, in a repeating manner, $-SO_3^-$ (polyethylene sulfonate, polystyrene sulfonate, etc.), $-OSO_3^-$ (polyvinylsulfate, polydestrane sulfate, etc.), $-O-PO_3^=$ and $-O-PO_3H^-$ (polyvinyl phosphate, etc.),

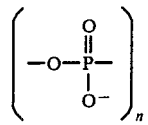

(polyphosphates, metaphosphates, etc.) groups. Representative examples of weak polyacid-derived polyanions are polymers or copolymers containing on the structure $-COO^-$ groups (polyacrylates, polymethacrylates, carboxymethyl cellulose, polygalacturonates, etc.).

As far as the molecular weight of the polyanion is concerned, the precipitation process of the salt with SAM is not critically controlled by this parameter. It is, in fact, observed that, in general, each polyanion is capable of giving rise, in an acid medium, to the formation of insoluble salts with SAM in a large range of molecular weights, an upper limit of which is the water-solubility of the polyanion and a lower limit of which is a degree of polymerization that should permit the molecule to fall into the class of polyelectrolytes (Doty P. et al., "Polymeric Electrolytes", Ann. Rev. Phys. Chem. 3, 81, 1952).

The mechanism of formation of these insoluble salts of SAM with polyanions may, in accordance with the present-day knowledge of the physicochemical character of polyelectrolytes, be reduced to two processes. The first process provides a stable interaction of SAM—via the positively charged sites thereof—with one molecule of the polyanion, the negative charges of which ar neutralized segments of several polymer chains, which results in the salt being precipitated. The second process mechanism provides for simultaneous interaction of one and the same molecule of SAM with the charged sites of different molecules of the polyanion to simultaneously bring about neutralization of the charges and an intermolecular crosslinking, two factors that are both conducive to salt precipitation. The relative role played by the two types of SAM-polyanion interaction in the formation of the insoluble salt is dependent upon the conditions of precipitation and the nature of the polyanion.

It is to be noted that both the processes involve a simultaneous, stable interaction of the various charged sites of SAM with negative charges that are defined topologically on the surface of the macroion.

In the case of the mols of SAM/equivalents of polyanion ratio of 1:3, the salts of the invention may be represented by the formula

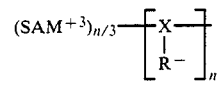

where the

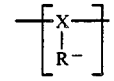

group may represent a group of formula

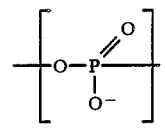

(poly- and meta-phosphates) or X may represent a group of the formula

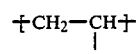

and $R^-$ one of the groups:

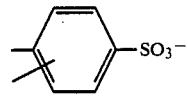

$-SO_3^-$, $-OSO_3^-$, $-OPO_3H^-$, $COO^-$.

The molecular weight of the polymer compound, and thus the value of n, is, as mentioned above, not critical except for the water-solubility of the polyanion and for it being able to fall into the class of polyelectrolytes.

The formula herein below gives a full, for the sake of clarity, the formula of SAM, the cation sites of which interact with the

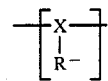

groups as previously defined, and which may, as set forth above, be a part either of a single polymer chain or of distinct molecules.

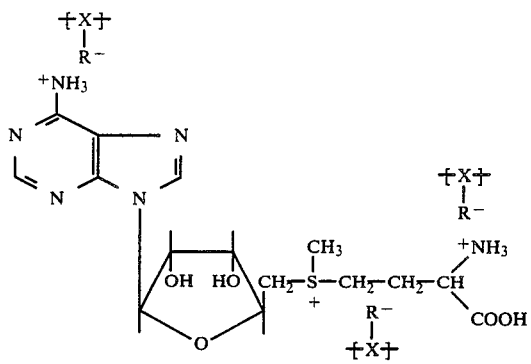

The salts of the present invention are particularly stable even at substantially higher temperatures than the room temperature: an analysis of their thermal stability versus time has, in fact, shown an unlimited stability of these compounds, when maintained in solid phase at 45° C. However, at 75° C., differentiated behaviors of the various salts prepared are observed with respect to one another. In any case, the stability at 75° C. exhibited by the salts of SAM with polyanions is generally far higher than that of all of the salts studied hitherto, the half-life times of which are, in the best case, shorter than 24 hours as compared with the up to 10~20-times higher values shown by the various salts of SAM with polyanions.

The salts of SAM with polyanions are solubilized in aqueous phase at pH >4 at a rate that is substantially controlled by the chemical nature of the polymer, the stoichiometry and physical characteristics of the solid salt, as well as the ionic strenght of the medium. The dissolution process does not involve any change in pH, even when conducted in poorly buffered media, due to the inherent low acidity of these salts.

In general, the lyophilized salts of SAM with polyanions are nonhygroscopic, white-colored, crystalline structured solids.

The precipitation of SAM from acid (preferred pH, 2.0 to 3.5) aqueous solutions is not affected even in the presence of high concentrations of neutral molecules, or molecules that are ionic in character. Moreover, it is highly specific, in that, for example, there is selectively precipitated SAM in the presence of MTA, one of the main degradation products of the sulfonium compound. It is possible for SAM with polyanions to be precipitated from extremely diluted solutions of the sulfonium compound (>0.001M), but closely packed precipitates being easily recovered by merely settling out, are obtained by the use of solutions of 0.002 to 0.2M concentrations. If required, improved yields in insoluble salts may be obtained by adding to the aqueous phase up to 1 volume of an organic, water-soluble solvent, such, for example, as methanol, ethanol, n-butanol, acetone, methyl ethyl ketone. Precipitation of SAM and the resultant stabilization thereof as a solid salt, are in general at an optimum when using 3 equivalents of the polyanion per mol of SAM in solution. Different stoichiometries utilizing a higher or lower ratio, are characterized by the presence in the precipitated salt, of other counter-ions from the medium. These will consist of cations, if the stoichiometric ratio of SAM to polyanion is lower than 0.33, and of anions if the ratio is higher than that value. THe precipitation of the salts of SAM with polyanions may be conducted by adding, under strong agitation, an aqueous solution of the polyanion to the solution of SAM, or conversely. The precipitate is quickly formed at room temperature, though a cooling down to 4° C. may, under certain circumstances, improve the yield in precipitate. According to the chemical nature of the polyanion, the precipitate appears to be in the form of a gel of varying consistency, which will quickly adhere to the vessel walls, or in the form of a large-sized, closely-packed particulate matter that, in most cases, allows for the liquors to be removed by simple decantation.

Following washing with water and, if desired, with organic solvents, the precipitated salt can be dried by vaporization by heat (preferred temperature, 50° C.) under vacuum, or by lyophilization. The grinding of the solid gives crystalline powders suitable for the use as active constituents in pharmaceutical formulations.

A variation to this general scheme, to be applied when SAM is precipitated from solutions containing other molecular species, as is the case with SAM-enriched yeast extracts, provides for solubilization of the precipitate at pH 5 in an adequate volume of water or buffer solution. In this way, the foreign molecular species remained trapped in the precipitate, are diluted throughout the volume. The salt of SAM with polyanions is then formed again by bringing down the pH of the solution to 2–3.

Owing to their simple conception and low costs, the procedures described in this invention easily lend themselves to working out methods of preparation on an industrial scale.

The examples given herein below illustrate the preparation of a series of salts of SAM with polyanions. Obviously, only a few of the many possible embodiments that may be anticipated, are shown by these examples which are intended to define, in a non-limiting sense, the scope encompassed by the invention. The examples refer to precipitations operated on solutions of SAM of different concentrations, though the method of procedure may find direct application also to the extracts of yeasts enriched with SAM.

EXAMPLE 1

To 10 liters of SAM sulfate, 40 mM, pH 2.0 by $H_2SO_4$, there are added at room temperature under strong stirring, 2 liters of a 0.6N solution of poly-para-styrene sulfonic acid (Mw $7 \times 10^4$), whose pH was adjusted to 2 (equivalent weight of the polyacid, 814). A milky emulsion is observed to form at once and coagulates in a few minutes to a mass of gummy consistency.

The liquors are removed by simple decantation and the precipitate is washed twice with 10 l of distilled $H_2O$ while keeping the system under strong stirring. After removing the washing water by decantation, the precipitate is dried under vacuum to give 342 g of a white, nonhygroscopic, crystalline product that is finely ground. The product thus produced is insoluble in water at pH <4, whereas increasing solubility is observed at pH of from 4 to 7. The UV spectrum of the salt in aqueous solution at ph of 4 shows a maximum at 258 nm coinciding with that of SAM. The high values of the coefficient of molar extinction of the adenine chromophore and its spectral superimposition with the benzene chromophore of the polyanion, prevent this structural component of the salt from being made apparent in the UV spectrum.

The HPLC analysis (Zappia V. et al., "Methods in Enzymology", 94, 57, 1983) (ULTRASIL CX 25 cm×4.6 mm i.d. cationic column, ammonium formate eluent, 0.5M, pH 4, flow rate, 1 ml/min) of the salt of SAM with the polyparastyrene sulfonate, in solution in the elution buffer, shows the presence of a chromatographic peak with the same retention time as that of SAM at 6.6 min., whose integration enables to state that the sulfonium compound represents about 40% of the dry weight of the precipitated salt. The $^1$H-NMR ($^2$H$_2$O; pH 7,0) spectroscopy of the salt of SAM with the polyparastyrene sulfonate shows, in the correct integration relationship, respectively the signals of SAM centered at $\delta$ 8.2; 6.0; 4.5; 3.9; 3.5; 2.7; and 2.3 and of the polyanion as enlarged signals respectively centered at $\delta$ 7.5; 6.5; and 1.5.

A rating of the relative relationship of integrals of the best resolved signals of the polyanion and of SAM enables to set at about 0.3 the ratio of mols of SAM to equivalents of polyparastyrene sulfonate in the salt.

The salt dissolves slowly at pH of from 4 to 5 whereas it is quickly solubilized at pH of 7.

The solubilization of 0.1 mol of SAM, in the form of salt with the polyparastyrene sulfonate, in 1 liter of phosphate buffer, pH 7, 0.01M, does not bring about any significant change in pH, thereby showing a negligible residual acidity of the precipitated salt.

Stability of the salt at 45° C. is unlimited in duration, while at 75° C. the half-life time is longer than one month.

EXAMPLE 2

To 1 liter of SAM sulfate, 20 mM, pH 2.5 by H$_2$SO$_4$, there are charged at ambient temperature, under strong stirring conditions, 500 ml of a 0.12N solution of sodium polyparastyrene sulfonate 5×10$^4$=Mw, whose pH had been adjusted to 2.5 (equivalent weight of the salt, 206). Precipitation reaction takes place as in Example 1. Washing and lyophilizing result in the production of 16.5 g of a white, nonhygroscopic, crystalline solid with spectroscopy, analysis and stability characteristics similar to those of the compound from Example 1, except that an increase in solubilisation times in experienced at pH >4.

EXAMPLE 3

To 10 liters of a 0.1N solution in NaClO$_4$ containing 0.3 mol of SAM perchlorate, adjusted to pH 2 with HClO$_4$, there are added at room temperature under strong agitation, 2 liters of a 0.45N solution of polyparastyrene sodium sulfonate, 6×10$^6$ Mw, whose pH had been adjusted to 2 (equivalent weight of the salt, 206). Evolution of the precipitation reaction is similar to that in Example 1. Following washing and lyophilization, 271 g of a white, nonhygroscopic, crystalline solid is obtained which is similar in spectroscopy, analysis and stability characteristics to the compound from Example 1, the only difference being in the slower rate of solubilization at pH>4.

EXAMPLE 4

To 1 liter of SAM sulfate, 0.1M, pH 2.0 via H$_2$SO$_4$, there are charged at room temperature and with strong stirring, 0.5 liters of a 0.6N solution of sodium polyvinylsulfonate, 2×10$^3$ Mw whose pH has been adjusted to 2 (equivalent weight of the salt, 130).

Formation of a milky emulsion is observed, and the emulsion tends to coagulate onto the reactor vessel walls to give a clear very viscous gel. Lowering the temperature down to 4° C. promotes this process thus allowing for the liquors to be removed by decantation.

Washing and lyophilization conducted as in Example 1, lead to the obtention of a white, nonhygroscopic, crystalline solid. Yield 61.1 g.

The product solubilizes rapidly at pH>4. The UV spectrum of the salt of aqueous solution at pH 6 is identical with that of SAM, with a maximum at 258 nm.

The analysis via HPLC of the salt, effected as described in Example 1, shows the presence of a single absorption UV peak, with the same retention time as that of SAM, the integration of which enables to state that the sulfonium compound represents about 55% of the dry weight of the precipitated salt.

The NMR spectroscopy ($^2$H$_2$O; pH 5.4) of the salt of SAM, shows, in a corrent integration relationship, that near the signals of SAM centered at $\delta$ 8.5; 8.4; 6.2; 4.6; 4.0; 3.6; 3.0 and 2.4, there are enlarged signals centered at $\delta$ 2.0 and 3.5 being imputable to the aliphatic chain of the polyanion. By comparing the integrals of these latter hydrogens with those of the better resolved protons of SAM, it may be stated that the ratio of moles of SAM to equivalents of polyanion in the salt is about 0.3. The residual acidity is, in accordance with what seen in Example 1, negligible, the stability of the solid salt at 45° C. is unlimited, while at 75° C. a half-life time of more than one month may be stated.

EXAMPLE 5

To 5 liters of SAM sulfate, 30 mM, pH 2.5 via H$_2$SO$_4$, there are added at room temperature and under strong stirring, 3 liters of a 0.15N solution of sodium polyvinylphosphate, Mw~1×10$^5$, whose pH had been adjusted to 2.5 (equivalent weight of the salt, 168). A slow flocculation is observed which can be accelerated by cooling the solution down to 4° C. Over about 2 hours, an adequate closely packed precipitated is formed and can be recovered by centrifugation at a slow rate or by filtration. Washing and lyophilizing the product as in Example 1 give 81 g of white, nonhygroscopic, crystalline solid. The product is rapidly solubilized at pH 7 and the HPLC analysis conducted as in Example 1, shows the presence of a single absorption UV peak, with the same retention time as that of SAM, the integration of which enables to state that the sulfonium compound represents about 60% of the dry weight of the precipitated salt. The UV spectrum of the salt in aqueous solution at pH of 6 is identical with that of SAM.

The NMR spectroscopy shown a similar picture to that given in Example 4, except for the chemical shift values of methylene and methine of the polymer backbone which, in this case, are in the form of enlarged signals centered on $\delta$ 2.0 and 4.6. Based on a comparison of the integrations of the protons of the sulfonium compound and the polyanion, the ratio of mols of SAM to equivalents of polyanion may be stated to be about 0.5.

The residual acidity, in accordance with what described in Example 1, is negligible, the stability of the solid salt at 45° C. is unlimited in duration, while at 75° C. a half-life time of more than 10 days may be stated.

EXAMPLE 6

To 10 liters of SAM sulfate, 0.01M, pH 2.5 via H$_2$SO$_4$, there are charged at 4° C. under strong stirring conditions, 2 liters of a 0.15N solution of sodium hexametaphosphate, whose pH was adjusted to 2.5 (equivalent weight of the sodium hexametaphosphate, 102). A white emulsion is observed to form quickly and, over 2~4 hours, it coagulates to a translucent gel very viscous in character which sticks to the reaction vessel walls thereby allowing for the liquors to be removed by decantation. Washing and lyophilization conducted as in Example 1, lead to the production of 53 g of a white, nonhygroscopic, crystalline solid. The product solubilizers rapidly at pH 7, the HPLC analysis, as to Example 1, showing the presence of a single UV absorption peak, with the same time of retention as that of SAM, the integration of which enables to state that the sulfonium compound represents about 63% of the dry weight of the precipitated salt. The UV and NMR spectra of the salt in aqueous solution, at pH 6, are identical with those of SAM.

The determination of the amount of phosphate in the salt, carried out on the hydrolyzed acid of the crystalline product, corroborates a stoichiometry of 1:3, defined as mols of SAM/equivalents of hexametaphosphate.

The residual acidity, is, in accordance with what seen in Example 1, negligible, the stability at 45° C. of the solid salt is unlimited in duration, while at 75° C. the half-life time may be stated as being of about 10 days.

EXAMPLE 7

To 5 liters of SAM sulfate, 0.02M, pH 2.5 via $H_2SO_4$, there are added at 4° C. with strong stirring, 0.5 l of a 0.6N solution of polyphosphoric acid (equivalent weight, 80; total contents in $P_2O_5$, 89%) prepared by dissolving in 100 g of $H_3PO_4$ 154 g of $P_2O_5$ and heating at 100° C. for 24 h. The polyphosphoric acid is then dissolved at 4° C. in water, the pH being quickly adjusted to pH 2.5 with NaOH.

The course of the reaction is similar to that in Example 6. Yield: 54 g of salt.

The spectroscopy and analysis characteristics, as well as the stability of the solid salt, are in accordance with what reported in Example 6.

EXAMPLE 8

To 10 liters of SAM sulfate, 0.1 m, pH 2.5 by added $H_2SO_4$, there are charged at 4° C. under strong stirring, 2 l of a 1.5N solution of polyphosphoric acid, Mw~$2\times 10^3$ (equivalent weight, 80), pH 2.5. The course of reaction is similar to that in Example 6. Yield, 518 g of salt.

The characterization as to the spectroscopy and analysis of the solid salt, as well as the stability of this latter, are in accordance with what reported in Example 6.

EXAMPLE 9

To 5 liters of SAM sulfate, 40 mM, pH 2.0 via $H_2SO_4$, there are added under strong stirring, 0.5 liters of a 1.2N solution of polyacrylic acid ($2.5\times 10^5$ Mw), whose pH was adjusted to 3.0 (equivalent weight of the polyacid, 72). A white coloured, gummy precipitate is observed to form instantly and sticks to the reactor vessel walls, thus enabling the mother liquors to be removed by decantation.

Washing and lyophilization are conducted as in Example 1 and lead to the production of 102 g of a white, nonhygroscopic, crystalline solid. The product solubilizes rapidly at pH 6 and the HPLC analysis, effected as described in Example 1, shows the presence of a UV absorption peak, with the same retention time as that of SAM, the integration of which enables to state that the sulfonium compound enters for about 60% in the dry weight of the precipitated stalt. The UV spectrum of the salt in aqueous solution at pH 6 is identical with that of SAM. MNR spectroscopy shows a picture similar to that reported in Example 4, except for the chemical shift values of the methylene and the methine of the polymer backbone which, in the instant case, appear as enlarged signals, centered at $\delta 1.8$ and 2.2. On the basis of a comparison between the integrations of protons of the sulfonium compound and the polyanion, it may be stated that the ratio of mols of SAMS to equivalents of the polyanion is 1:3. The residual acidity is, in accordance with Example 1, negligible, the stability of the solid salt at 45° C. is unlimited in duration, while a half-life of about 20 hours may be stated for the solid salt at 75° C.

EXAMPLE 10

Thermal stability at 75° C. in solid phase

The thermal stability at 75° C. in solid phase, of the salts prepared in Examples 1, 3, 4, 5, 6, 7 and 9 has been compared with that of SAM chloride and the double salt of formula $SAM^+.HSO_4^-.H_2SO_4.2CH_3C_6H_4SO_3H$. From the results that are given in the figure of the annexed drawing as percent degradation of SAM versus the time, the higher stability of the salts according to the invention is clearly apparent.

The salts of SAM prepared in conformity to this invention, have substantially the same toxicity as that of the sulfonium compound containing counterions of a nonpolyelectrolyte type.

In order to evaluate the pharmacokinetics and bioavailability properties of the salts of the invention, the salts of S-adenosyl-L-(met-$^{14}$C)methionine with polyparastyrenesulfonate, polyphosphate and sulfate (as reference compound) were prepared by precipitating a solution of S-adenosyl-L-(Met-$^{14}$C)methionine having specific radioactivity of 2 $\mu$Ci/mol, with solutions of the polyanions as above described.

Male Wistar rats, divided in groups of 5 animals each, were treated by gastric tube with 10 mg/kg (equivalent to 10 $\mu$Ci from $^{14}$C) of active principle and sacrificed at different times (2, 8, 24 and 48 hours) from the administration.

Urine and feces were collected only at the 24th and 48th hour while blood samples were also drawn at 30' by the caudal vein. The liver, kidneys, small and large intestine, gastric and bowel contents, urine, feces, and plasma were collected and counted for radioactivity as dpm/g or dpm/ml.

The results obtained clearly show that the salts of the invention are effectively absorbed, with more than 60% of the radioactivity present in the administered dose which is absorbed and metabolized after 24 hours.

The polyparastyrenesulphonate and polyphosphate salts, being insoluble in acidic medium, ar not absorbed at the gastric level where the residence time is less than 2 hours and shorter than SAM-sulfate.

The stable salts of SAM with polyanions are solubilized at the intestinal level already in the small intestine, where the absorption process starts. Generally, the absorption of the radioactivity connected with the active principle as salt with polyparastyrenesulfphonate and polyphosphate is superimposable to what is found for SAM sulfate. The novel salts of SAM with polyanions can, therefore, be conveniently employed in pharmaceutical preparations intended for oral or parenteral administration.

Owing to their poor solubility in acid media, the salts of SAM with polyanions when used in oral formulations behave as pharmacologic constituents of the gastro-protected, predominantly intestinal absorption type. When using non-biodegradable macromolecules such as the polystyrene sulfonates, polyvinil sulfonates, polyvinyl phosphates, etc., the preferred polyanions are those having such sufficiently high molecular weight as to not be subject to intestinal absorption so that they are effectively eliminated as fecal waste material.

In intravenous formulations, the preferred salts of SAM with polyanions are those with polyanions that are quickly biodegradable "in vivo" to nontoxic molecular species, such, for example, as the polyphosphates which are effectively degraded to inorganic phosphate by the pyrophosphatases present inthe organism. The salt of SAM with hexametaphosphate is a representative example of a compound that can be efficiently used for parenteral administration, following to solubilization in an appropriate buffer of low molarity.

The following are examples of pharmaceutical formulations containing the salts of the invention as active constituents:

Tablets or capsules containing from 20 to 200 mg of active constituent, expressed as sulfonium compound, together with appropriate excipients such as starch, magnesium stearate, lactose, talc;

Lyophilized ampules for intravenous or intramuscular injection, containing from 20 to 500 mg of active constituent expressed as the sulfonium compound, for use in conjunction with appropriate sterile or apyrogen solvents, which may contain analgesics, buffering agents, etc.;

Suppositories containing from 50 to 500 mg of active constituent expressed as the sulfonium compound, together with excipients conventionally used for rectal applications.

The compositions of the invention can be administered for all the indications peculiar to SAM, at the rate of 1–2 times a day by parenteral administration and of 2–4 times a day by oral administration, according to the diagnosis, the weight and the conditions of a patient.

We claim:

1. A salt of S-adenosyl-L-methionine and a water-soluble polyanionic substance selected from the group consisting of a polyphosphate, metaphosphate, polystyrene sulfonate, polyvinyl sulfonate, polyvinyl sulfate, polyvinyl phosphate, and polyacrylate wherein the stoichiometric ratio of mols of S-adenosyl-L-methionine to gram-equivalent of the polyanionic substance is from 0.1:1 to 0.5:1.

2. A salt of S-adenosyl-L-methionine according to claim 1 wherein the polyanionic substance is a polyphosphate or metaphosphate.

3. A salt of S-adenosyl-L-methionine according to claim 1 wherein the polyanionic substance is a para-polystyrene sulfonate.

4. A salt of S-adenosyl-L-methionine according to claim 1 wherein the stoichiometric ratio of S-adenosyl-L-methionine to gram-equivalent of the polyanionic substance is about 0.33:1.

5. A process for the preparation of a salt of according to claim 1 which comprises the steps of (a) mixing a solution of S-adensoyl-L-methionine at acidic pH with a solution of the polyanionic substance wherein the stoichiometric ratio of S-adenosyl-L-methionine to gram-equivalent of the polyanionic substance is from 0.1:1 to 0.5:1, at the same pH while stirring at room temperature, (b) collecting the salt thus formed, (c) washing the collected salt with water, and (d) drying the salt under vacuum or by lyophilization.

6. The process according to claim 5 wherein step (a) is carried out by having S-adenosyl-L-methionine precipitated from extracts of yeast cells enriched with S-adenosyl-L-methionine.

7. The process according to claim 6 wherein prior to drying, the precipitate formed is first dissolved at pH of from 4 to 5 in an adequate volume of water and is then precipitated again by lowering the pH of the solution.

8. The process according to claim 5 wherein step (a) is conducted at 4° C.

9. The process according to claim 5 wherein, at the end of the precipitation in step (a), there is added up to 1 volume of an organic, water-miscible solvent to the aqueous phase.

10. The process according to claim 5 wherein, in step (b), the precipitate is washed by grinding in organic solvents.

11. A pharmaceutical composition comprising an effective amount of at least one salt according to claim 1 in combination with at least one compatible, nontoxic excipient.

12. A pharmaceutical composition according to claim 11 in the form of a capsule, tablet, sugar-coated pill, an ampule of intravenous or intramuscular injectable solution, or suppository.

* * * * *